(12) United States Patent
Valax et al.

(10) Patent No.: US 7,741,455 B2
(45) Date of Patent: Jun. 22, 2010

(54) METHOD FOR PURIFYING FSH

(75) Inventors: Pascal Valax, Chernex (CH); Pierre Wenger, Grilly (FR); Anne Stanley, Rotorua (NZ); Lydia Delegrange, Lutry (CH); Luciano Capponi, Chatel Saint-Denis (CH)

(73) Assignee: Ares Trading SA, Aubonne (CH)

( * ) Notice: Subject to any disclaimer, the term of this patent is extended or adjusted under 35 U.S.C. 154(b) by 395 days.

(21) Appl. No.: 11/575,833

(22) PCT Filed: Nov. 8, 2005

(86) PCT No.: PCT/EP2005/055815
§ 371 (c)(1),
(2), (4) Date: Mar. 22, 2007

(87) PCT Pub. No.: WO2006/051070
PCT Pub. Date: May 18, 2006

(65) Prior Publication Data
US 2008/0070832 A1 Mar. 20, 2008

Related U.S. Application Data

(60) Provisional application No. 60/628,717, filed on Nov. 17, 2004.

(30) Foreign Application Priority Data
Nov. 9, 2004 (EP) .................................. 04105639

(51) Int. Cl.
C07K 1/14 (2006.01)
C07K 1/16 (2006.01)
C07K 1/18 (2006.01)
C07K 1/20 (2006.01)
C07K 1/22 (2006.01)
C07K 1/36 (2006.01)
C07K 14/59 (2006.01)

(52) U.S. Cl. .................... 530/412; 530/395; 530/397; 530/398; 530/416; 530/359; 530/413

(58) Field of Classification Search .................. None
See application file for complete search history.

(56) References Cited
U.S. PATENT DOCUMENTS 5,567,677 A 10/1996 Castensson et al.
5,990,288 A 11/1999 Musick et al.
6,162,905 A 12/2000 Lualdi et al.
2003/0171267 A1* 9/2003 Rosen et al. ................. 514/12
2003/0186893 A1 10/2003 Paradisi et al.
2007/0129295 A1 6/2007 Rossi

FOREIGN PATENT DOCUMENTS

| CA | 2399100 | * | 8/2001 |
| EP | 0475779 | A1 | 3/1991 |
| EP | 1106623 | A1 | 11/1999 |
| EP | 1247818 | * | 10/2002 |
| WO | WO 88/10270 | | 12/1988 |
| WO | WO 96/25496 | | 8/1996 |
| WO | WO 97/29767 | | 2/1997 |
| WO | WO 98/20039 | | 5/1998 |
| WO | WO 00/63248 | | 10/2000 |
| WO | WO 2005/063811 | A1 | 4/2005 |
| WO | WO 2006/016960 | A2 | 2/2006 |

OTHER PUBLICATIONS

Bell et al., Proc Soc Exp Biol Med. 1975; 149: 565-9.*
Handbook of HPLC—Chromatographic Science Series (vol. 78 Edited by E. Katz, R. Eksteen, P. Schoenmakers and N. Miller Marcel Dekker Inc., New York, USA, 1998 pp. 989 ISBN 0-8247-9444-3; pp. 463-482.*
Nomura et al., Proc Natl. Acad Sci. 1982; 79: 6675-6679.*
Office Action mailed Mar. 18, 2009 in U.S. Appl. No. 10/581,172, filed Feb. 6, 2007.
Tikhomirov, M.M. et al. "High-Performance Liquid Chromatographic Investigation of the Amino Acid, Amino Sugar and Neutral Sugar Content in Glycoproteins", *Journal of Chromatography*, 1978, pp. 197-203, vol. 167.
Lowry, O.H. et al. "Protein Measurement with the Folin Phenol Reagent", *The Journal of Biological Chemistry*, May 28, 1951, pp. 265-275, vol. 193.
Lynch, S. et al. "The extraction and purification of human pituitary follicle-stimulating hormone and luteinizing hormone" *Acta Endocrinologica (Copenh)*, 1988, pp. 12-19, vol. 288.
Chiba, K. et al. "Isolation and Partial Characterization of LH, FSH and TSH from Canine Pituitary Gland" *Endocrine Journal*, 1997, pp. 205-218, vol. 44, No. 2.

* cited by examiner

*Primary Examiner*—Bridget E Bunner
*Assistant Examiner*—Christina Borgeest
(74) *Attorney, Agent, or Firm*—Saliwanchik, Lloyd & Saliwanchik

(57) ABSTRACT

The invention relates to a method for purifying recombinant human FSH or an FSH variant starting from crude FSH, comprising the following steps: 1) dye-affinity chromatography; 2) hydrophobic interaction chromatography; and 3) reverse phase chromatography.

5 Claims, 2 Drawing Sheets

SEQUENCE LISTING

<160> NUMBER OF SEQ ID NOS: 5

<210> SEQ ID NO 1
<211> LENGTH: 91
<212> TYPE: PRT
<213> ORGANISM: Homo sapiens

<400> SEQUENCE: 1

```
Ala Pro Asp Val Gln Asp Cys Pro Glu Cys Thr Leu Gln Glu Asn Pro
1               5                  10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Val Glu Asn His Thr Ala
65                  70                  75                  80

Cys His Cys Ser Thr Cys Tyr Tyr His Lys Ser
                85                  90
```

<210> SEQ ID NO 2
<211> LENGTH: 129
<212> TYPE: PRT
<213> ORGANISM: Homo sapiens

<400> SEQUENCE: 2

```
Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
            35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
                100                 105                 110

Thr Val Arg Gly Leu Gly Pro Ser Tyr Cys Ser Phe Gly Glu Met Lys
            115                 120                 125

Glu
```

```
<210> SEQ ID NO 3
<211> LENGTH: 108
<212> TYPE: PRT
<213> ORGANISM: Homo sapiens

<400> SEQUENCE: 3

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
            35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu
            100                 105
```

```
<210> SEQ ID NO 4
<211> LENGTH: 106
<212> TYPE: PRT
<213> ORGANISM: Homo sapiens

<400> SEQUENCE: 4

Asn Ser Cys Glu Leu Thr Asn Ile Ala Ile Glu Lys Glu Glu Cys Arg
1               5                   10                  15

Phe Cys Ile Ser Ile Asn Thr Trp Cys Ala Gly Tyr Cys Tyr Thr Arg
            20                  25                  30

Asp Leu Val Tyr Lys Asp Pro Ala Arg Pro Lys Ile Gln Lys Thr Cys
            35                  40                  45

Thr Phe Lys Glu Leu Val Tyr Glu Thr Val Arg Val Pro Gly Cys Ala
    50                  55                  60

His His Ala Asp Ser Leu Tyr Thr Val Pro Val Ala Thr Gln Cys His
65                  70                  75                  80

Cys Gly Lys Cys Asp Ser Asp Ser Thr Asp Cys Thr Val Arg Gly Leu
```

-continued

```
                        85                  90                  95
Gly Pro Ser Tyr Cys Ser Phe Gly Glu Met
                100                 105

<210> SEQ ID NO 5
<211> LENGTH: 110
<212> TYPE: PRT
<213> ORGANISM: Homo sapiens

<400> SEQUENCE: 5

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
                20                  25                  30

Tyr Thr Arg Asp Leu Val Tyr Lys Asp Pro Ala Arg Pro Lys Ile Gln
            35                  40                  45

Lys Thr Cys Thr Phe Lys Glu Leu Val Tyr Glu Thr Val Arg Val Pro
        50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys
                100                 105                 110
```

METHOD FOR PURIFYING FSH

CROSS-REFERENCE TO RELATED APPLICATION

This application is the U.S. national stage application of International Patent Application No. PCT/EP2005/055815, filed Nov. 8, 2005, which claims the benefit of U.S. Provisional Patent Application No. 60/628,717, filed Nov. 17, 2004, the disclosures of which are hereby incorporated by reference in their entireties, including all figures, tables and amino acid or nucleic acid sequences.

FIELD OF INVENTION

The invention relates to the field of the purification of follicle stimulating hormone (FSH).

BACKGROUND OF THE INVENTION

Follicle-stimulating hormone (FSH) is an injectable protein falling into the class of gonadotrophins. FSH is used in the treatment of infertility and reproductive disorders in both female and male patients.

In nature, FSH is produced by the pituitary gland. For pharmaceutical use, FSH may be produced recombinantly (rFSH), or it may be isolated from the urine of postmenopausal females (uFSH).

FSH is used in female patients in ovulation induction (OI) and in controlled ovarian hyperstimulation (COH) for assisted reproductive technologies (ART). In a typical treatment regimen for ovulation induction, a patient is administered daily injections of FSH or a variant (about 75 to 300 IU FSH/day) for a period of from about 6 to about 12 days. In a typical treatment regimen for controlled ovarian hyperstimulation, a patient is administered daily injections of FSH or a variant (about 150-600 IU FSH/day) for a period of from about 6 to about 12 days.

FSH is also used to induce spermatogenesis in men suffering from oligospermia. A regimen using 150 IU FSH 3 times weekly in combination with 2'500 IU hCG twice weekly has been successful in achieving an improvement in sperm count in men suffering from hypogonadotrophic hypogonadism [Burgues et al.; *Subcutaneous self-administration of highly purified follicle stimulating hormone and human chorionic gonadotrophin for the treatment of male hypogonadotrophic hypogonadism. Spanish Collaborative Group on Male Hypogonadotrophic Hypogonadism; Hum. Reprod.;* 1997, 12, 980-6].

Because of the importance of FSH in the treatment of fertility disorders, the provision of FSH of high purity and high specific activity is desirable. FSH treatment requires repeated injections. Highly purified FSH preparations can be administered subcutaneously, permitting self-administration by the patient, thus increasing patient convenience and compliance.

Lynch et al. [The extraction and purification of human pituitary follicle-stimulating hormone and luteinising hormone; *Acta Endocrinologica*, 1988, 288, 12-19] describe a method for purifying human pituitary FSH. The method involves anion and cation exchange chromatography, immunoaffinity extraction and size exclusion chromatography. The method is said to result in pituitary FSH having a specific activity of 4,990 IU (immunoassay)/mg, with 16 IU/mg of LH. Protein content was determined either by dry weight or in solution by absorption at 280 nm (assuming that $A_{1\ cm}^{280}$ for 1 g/l is equal to 1).

WO 98/20039 (IBSA Institut Biochimique SA) describes a process for the purification of human urinary FSH starting with urinary extracts called human menopausal gonadotrophins (hMG). The process uses ion-exchange chromatography on weakly basic anionic exchange resins of the DEAE type followed by affinity chromatography on resin having an anthraquinone derivative as a ligand. The process is said to yield urinary FSH free from LH and having a specific activity of 6,870 IU (immunoassay)/mg. Protein content was determined by assuming that a water solution of 1 mg/ml of protein has an optical density of 0.62 at 277 nm, in quartz cuvettes with a 1 cm path length.

WO 00/63248 (Instituto Massone SA) describes a process for the purification of gonadotrophins, including FSH, from human urine. The process involves the following steps: ion exchange chromatography with a strong cationic resin of the type sulphopropyl, ion exchange chromatography with a strong anionic resin, and hydrophobic interaction chromatography (HIC). A FSH preparation having a specific activity of 8,400 IU/mg (Steelman-Pohley method: *Assay of the follicle stimulating hormone based on the augmentation with human chorionic gonadotrophin; Endocrinology;* 1953, 53, 604-616) and less than 1 IU LH (rat seminal vesicle weight gain method: Van Hell H, Matthijsen R & G A Overbeek; *Acta Endocrinol,* 1964, 47, 409) biological activity per 75 IU FSH is reportedly obtained. Protein content was performed by the Lowry method [O. H. Lowry et al., *J. Biol. Chem.*, 1951, 193, 265].

U.S. Pat. No. 5,990,288 (Musick et al.) describes a method for purifying FSH from biological samples, such as human pituitary glands or human post-menopausal urine. The process uses cation exchange chromatography on Fractogel EMD $SO_3$-650M, followed by dye affinity chromatography on Mimetic Orange 1 resin, followed by a step of hydrophobic interaction chromatography on Bakerbond Wide Pore HI-Propyl resin. The process is said to result in human pituitary FSH having a specific activity of 7,066 IU (immunoassay)/mg and less than 1 IU (immunoassay)/mg of LH, and a urinary FSH having a specific activity of 6,298 IU (immunoassay)/mg and less than 3 IU (immunoassay)/mg of LH. Protein content was determined by absorption at 280 nm (assuming that $A_{1\ cm}^{280}$ for 1 g/l is equal to 1).

Chiba et al. [Isolation and partial characterisation of LH, FSH and TSH from canine pituitary gland; *Endocrinol. J.,* 1997, 44, 205-218] describe a technique for purifying canine pituitary gonadotrophins, including FSH, using Concanavalin (Con) A affinity chromatography, hydrophobic interaction chromatography (HIC) and immobilized metal ion chromatography with $Cu^{++}$. The resulting FSH is reported to have a specific activity of 2.17 IU/g protein using a radioreceptor assay for FSH for measuring biological activity and the Bio-Rad protein assay kit (BioRad Laboratories CA USA) for determining protein content.

WO 88/10270 (Instituto di Ricerca Cesare Serono SPA) describes a method for purifying human FSH from urine. The process involves immunochromatography with FSH-specific immobilized monoclonal antibodies bound to Sepharose 4B by divinyl sulphone, followed by reverse phase HPLC. The resulting FSH is free of LH and other urinary proteins and has a specific activity of 6,200 IU/mg of lyophilised powder (Steelman-Pohley method). The preparation was the first FSH preparation to be suitable for subcutaneous administration, due to its purity.

An ongoing need remains for new methods for purifying FSH and FSH variants. In particular, there is a need for purification methods that avoid the use of the cost-intensive immunoaffinity chromatography steps.

SUMMARY OF THE INVENTION

It is an object of the invention to provide a new method for purifying recombinant FSH or a recombinant FSH variant.

In a first aspect, the invention provides a method for purifying recombinant human FSH or an FSH variant starting from a liquid containing the crude FSH, comprising the following steps:
 (1) dye-affinity chromatography;
 (2) hydrophobic interaction chromatography; and
 (3) reverse phase chromatography;

which may be carried out in any order.

ABBREVIATIONS

Figure 1:
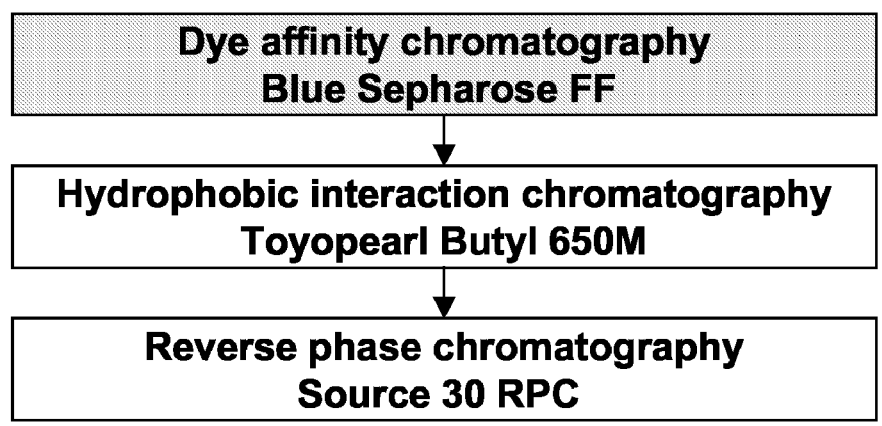
FIG. 1 illustrates the present invention, i.e. a process of purification comprising the steps of:
 dye affinity chromatography,
 hydrophobic interaction chromatography,
 reverse phase chromatography.

The following abbreviations are used in the description of the invention:
DF: diafiltration
FSH: follicle stimulating hormone;
r-FSH: recombinant FSH;
hFSH: human FSH;
r-hFSH: recombinant human FSH
BV: Bed volume
DEAE: diethylaminoethyl
ELISA: enzyme linked immunoassay
DAC: dye affinity chromatography
IMAC: immobilised metal ion affinity chromatography
OD: optical density
HIC: Hydrophobic interaction chromatography
HPLC: high performance liquid chromatography
IRMA: immunoradiometric assay
KD or kD: kiloDalton
HCP: host cell protein, proteins arising from the host cell used for expression of FSH
IPC: In process controls
IEF: isoelectric focussing
PES: polyethersulphone
RP-HPLC: reverse phase high performance liquid chromatography
Q FF: anion exchange on Q Sepharose FF
RT: Room Temperature
UF: ultrafiltration
WFI: water for injection

DETAILED DESCRIPTION OF THE INVENTION

The invention provides a method for purifying recombinant human FSH or a recombinant FSH variant starting from a liquid containing the crude FSH, comprising the steps:
 (1) dye affinity chromatography;
 (2) hydrophobic interaction chromatography; and
 (3) reverse phase chromatography;

which may be carried out in any order.

The purification method of the invention affords a recombinant FSH bulk of high purity which may then be formulated to the final medicament, e.g. Gonal-F (Serono). It has the advantage of affording a high degree of purity without using immunoaffinity chromatography. The crude FSH which forms the starting material for the purification according to the present invention consists in cell culture harvests containing recombinant FSH.

In a preferred embodiment, an antioxidant or a free amino acid or dipeptide with antioxidant and scavenging effect is included in some or all of the steps of the purification method according to the present invention. More precisely, the antioxidant is present in any of the buffers used to purify and/or concentrate and/or filter the r-hFSH. The antioxidant prevents oxidation of the FSH during processing. A preferred antioxidant is L-methionine. Preferably, L-methionine is used at a concentration of at or about 10-100 mM. Further examples of an antioxidant include t-butyl-4-methoxy-phenol, 2,6-bis(1,1-dimethylethyl)-4-methyl phenol; potassium or sodium bimetabisulfite, sodium bisulfite. Examples of free amino acid and dipeptide with antioxidant and scavenging effect are histidine, taurine, glycine, alanine, carnosine, anserine, 1-methylhistidine or combinations thereof.

Typically, the starting material is clarified first and then and optionally concentrated (e.g. by using ultrafiltration) and/or buffer exchanged (e.g. through a diafiltration step) prior to being captured on the first chromatographic step.

In the steps of chromatography, polymer-based and agarose-based resins may be used. It is also possible to use membrane chromatography, in which the resin is replaced with a functionalised membrane.

The 3 purification steps of the present invention (i.e. dye affinity chromatography, hydrophobic interaction chromatography, reverse phase chromatography) are in the following outlined more in detail.

The Dye Affinity Chromatography Step (1)

The method of the invention involves a step of dye affinity chromatography (1). In a preferred embodiment, the step of dye affinity chromatography is carried out using a resin having as an immobilised ligand a dye compound which is well known to a person skilled in the art, i.e. Cibacron Blue F3G-A. The term "immobilized" is well understood by a person skilled in the art and means that the ligand is derivatised in the sense that it is chemically linked to the resin. A particularly preferred resin is Blue Sepharose FF (obtainable from Amersham Biosciences Inc.). The technical features of Blue Sepharose FF are as follows:

| TECHNICAL SPECIFICATIONS | |
|---|---|
| Ligand | Cibacron Blue F3G-A |
| Ligand coupling method | Triazine coupling |
| Binding capacity | =18 mg human serum albumin/ml drained gel |

-continued

| TECHNICAL SPECIFICATIONS | |
|---|---|
| Matrix | Highly cross-linked agarose, 6% |
| Exclusion limit ($M_r$) | $4 \times 10^6$ |
| Particle size range | 45-165 μm |
| Linear flow rate* | ≈750 cm/h |
| Ligand density | ≈7 μmol Cibacron Blue/ml medium |
| pH stability | 4-12 (long term), 3-13 (short term) |
| Chemical stability | 40° C. for 7 days in: 70% ethanol, 6 M guanidine hydrochloride, 8 M urea |

It is understood that the method may be performed with alternate resins, having similar characteristics. Examples of alternative resins include: Toyopearl AF-blue-HC-650M (Tosoh Bioscience), Toyopearl SuperButyl 550, Toyopearl Phenyl 650, Blue Cellthru BigBead (Sterogene), SwellGel Blue (Pierce), Cibachrome blue 3GA-agarose 100 (Sigma), Affi-Gel Blue (BioRad), Econo-Pac blue cartridges (Bio-Rad), Blue sepharose HP (Amersham), Cibacron Blue 3GA (Sigma).

Elution in the step of immobilised dye affinity chromatography should preferably be carried out using a buffer of phosphate, particularly preferably sodium phosphate. The pH of the eluent should preferably be at or about 6.0 to at or about 11.5, more preferably at or about 6.5 to at or about 8, particularly preferably at or about 7.0. Alternate buffers appropriate for maintaining a pH of 7.0 include the following: MES, Bis-Tris, ADA, PIPES, ACES, BES, MOPS, TES, HEPES. The elution buffer for the step of dye affinity chromatography should preferably contain a salt to increase the conductivity, preferably NaCl.

In a particularly preferred embodiment, the product-contacting buffers for the step of dye affinity chromatography (equilibration, wash and elution) contain an antioxidant, such as L-methionine. Further examples of an antioxidant include t-butyl-4-methoxyphenol, 2,6-bis(1,1-dimethylethyl)-4-methyl phenol; potassium or sodium bimetabisulfite, sodium bisulfite.

The Hydrophobic Interaction Chromatography Step (2)

The method also involves a step of hydrophobic interaction chromatography (2). In a preferred embodiment, the hydrophobic interaction chromatography is carried out with a resin such as Toyopearl Butyl 650M (obtainable from Tosoh Biosep Inc.).

It is understood that step (2) may be performed using alternate resins, having similar characteristics. Alternative resins that may be used are as follows: Phenyl Sepharose 6 Fast Flow (low sub); Phenyl Sepharose 6 Fast Flow (high sub); Butyl Sepharose 4 Fast Flow; Octyl Sepharose 4 Fast Flow; Phenyl Sepharose High Performance; SOURCE 15ETH; SOURCE 15ISO; SOURCE 15PHE all from Amersham Biosciences (800) 526-3593; (see www.amershambiosciences.com). Still further resins are: Hydrocell C3 or C4; Hydrocell Phenyl from BioChrom Labs Inc. (812) 234-2558; (see www.biochrom.com)

Binding on the HIC resin is achieved in a buffer with a high conductivity, obtained through the addition of salt (NaCl, $(NH_4)_2SO_4$ or $Na_2SO_4$ for example). Elution in the step of hydrophobic interaction chromatography is preferably carried out by reducing the conductivity of the mobile phase (reducing salt concentration), using a buffer having a pH at or about 6 to at or about 8, more preferably at or about 6.5 to at or about 7.5, most preferably at or about 7). A particularly preferred system contains sodium phosphate for buffering preferably at a pH of at or about 7, and ammonium sulfate. Alternative buffers are mentioned above.

In a particularly preferred embodiment, the product-contacting buffers for the step (2) of HIC (equilibration, wash, elution) contain an antioxidant, such as L-methionine. Alternative antioxidants are mentioned above.

The Reverse Phase Chromatography Step (3)

The method of the invention also comprises a step of reverse phase chromatography (RPC) (3). The RPC is preferably carried out using a resin such as SOURCE 30 RPC (obtainable from Amersham Biosciences). It is understood that step (3) may be performed using alternative resins which are well known to a person skilled in the art and which have similar characteristics.

The chromatography is preferably carried out using a mobile phase buffering at mildly alkaline pH, for example at or about pH 7-8.5, more preferably at or about 7.5 or 7.6. In a preferred embodiment, the buffering species is ammonium acetate. Alternate buffers adequate for a pH at or around 7.6 include: BES, MOPS, Phosphate, TES, HEPES. The buffer solutions used for this step may also contain an organic modifier, the concentration of which is modulated for different phases of the chromatography step (load, wash, elution and regeneration). In a preferred embodiment, the organic modifier is a water miscible organic solvent, preferably an alcohol (such as methanol, ethanol, etc.), most preferably 2-propanol (iso-propanol).

In a particularly preferred embodiment, the product-contacting buffers for the step of RPC (equilibration, wash, elution) contain an antioxidant, such as L-methionineAlternate antioxidants are mentioned above.

Optional Further Purification Step 0—Ion Exchange Chromatography

Further to the 3 main purification steps—outlined above—the present invention may include additional purification steps.

In one embodiment, the purification method of the invention involves a preliminary step of ion exchange chromatography (0) carried out, preferably with a strong anion exchange resin, particularly preferably a quaternary ammonium resin, such as Q Sepharose FF (obtainable from Amersham Biosciences), having the following characteristics:

| | |
|---|---|
| Type of ion exchanger: | Strong anion |
| Total capacity (mmol/ml): | 0.18-0.25 |
| Exclusion limit (globular proteins): | $4 \times 10^6$ |
| Bead form: | Spherical, diameter 45-165 μm |
| Bead structure: | Cross-linked agarose, 6% |
| Operational pH stability: | 2-12 |
| Cleaning pH stability: | 1-14 |
| Linear flow rate at 25° C. 1 bar 15 cm bed height, XK 50/30 column: | 400-700 cm/h |

Alternatively, the ion-exchange chromatography step (0) may be carried out using a resin such as Fractogel EMD TMAE HICAP (obtainable from Merck KGaA, Darmstadt Germany), or a resin having similar characteristics, see below:

| | |
|---|---|
| Support | Fractogel ® EMD TMAE |
| Cat. No. | 1.16887 |
| Particle size S-type | 20-40 μm |

| | |
|---|---|
| Type of chromatography | ion-exchange chromatography |
| Functional group | trimethylaminoethyl group (Q-type) |
| Monomer structure | $CH_2=CH—CONH—(CH_2)_2N + (CH_3)_3$ |
| Protein binding capacity | 120 mg BSA/ml of gel |
| pH stability range | pH 2 up to pH 12 |
| pK value | >13 |
| Elution conditions | high salt concentrations |
| Pressure limit (bed: 150 × 10 mm) | 20 bar (pressure drop along the column) |
| Working temperature | 4° C. to room temperature |
| Preservative | 20% ethanol |
| Ready to use cartridge | 50-10 mm |
| Bulk material S-types | 100 ml; 500 ml |
| Linear flow rate | 1.27-6.35 cm/min |

The step of ion-exchange chromatography is preferably carried out using a buffer having a mildly alkaline pH (e.g. at or about 7.2 to at or about 9.0, or at or about 8.0 to at or about 9.0, most preferably at or about 8.5). Suitable buffers include, for example borate buffer, triethanolamine/iminodiacetic acid Tris, ammonium acetate, tricine, bicine, TES, HEPES, TAPS. Most preferred is borate buffer, at a pH of at or about 8.5. Elution from the ion-exchange resin is achieved by increasing the conductivity of the mobile phase through the addition of salt, preferably NaCl. In a particularly preferred embodiment the product-contacting buffers for the ion-exchange chromatography (equilibration, wash, elution) contain an antioxidant, preferably L-methionine. Alternative antioxidants are mentioned above.

Thus in a preferred embodiment, the method of the invention comprises the following steps:
- (0) anion-exchange chromatography, preferably on a strong anion exchange resin, [preferably a quaternary ammonium resin, such as Q Sepharose FF or Fractogel EMD TMAE];
- (1) dye affinity chromatography [preferably on Blue Sepharose FF];
- (2) hydrophobic interaction chromatography [preferably on Toyopearl Butyl 650M];
- (3) reverse phase chromatography [preferably on Source 30 RPC].

Optional Further Purification Step (−1)—Ultrafiltration/Diafiltration

Prior to the step of ion exchange chromatography (0), it may be desirable to carry out a step of ultrafiltration, in order to concentrate the crude FSH. The ultrafiltration (or diafiltration) is preferably carried out using a membrane having a cut-off of at or about 3-10 kD, most preferably at or about 8 kD.

Optional Further Purification Step (4)—Anion-Exchange Chromatography

In a further preferred embodiment, the method of the invention also comprises a second step of anion-exchange chromatography (4). A preferred resin is Fractogel EMD TMAE HICAP (obtainable from Merck KGaA, Darmstadt Germany), or a resin having similar characteristics, as mentioned above. Alternatively the second step of anion-exchange chromatography may be carried out on Q Sepharose FF, or other resin having similar characteristics, as mentioned above.

The steps of anion exchange chromatography, dye affinity chromatography, hydrophobic interaction chromatography (HIC), reverse phase chromatography and second step of anion-exchange chromatography may be carried out in any order, although it is preferred to carry out a step of anion exchange chromatography first. The remaining steps of dye affinity chromatography, hydrophobic interaction chromatography (HIC), RPC and optional second anion-exchange chromatography may be carried out in any order, although it is preferred to follow the order shown below:

(0) anion-exchange chromatography, (1) dye affinity chromatography, (2) hydrophobic interaction chromatography (HIC), (3) reverse phase chromatography RPC; and (4) second anion-exchange chromatography.

Optional Further Purification Step (5)—Ultrafiltration/Diafiltration

In a further preferred embodiment, after any of the steps of chromatography (particularly after a step of reverse phase chromatography), the FSH sample is subjected to a concentration step. Preferably the step is performed using ultrafiltration combined by diafiltration in order to obtain a bulk having the desired composition. The ultrafiltration (or diafiltration) is preferably carried out using a membrane having a cut-off of at or about 3-10 kD, most preferably at or about 5 kD.

In a particularly preferred embodiment, the following steps are carried out in the order shown below:
- (−1) Ultrafiltration (preferably with a membrane having a cut-off of at or about 8 kD),
- (0) anion-exchange chromatography (preferably using a Q Sepharose FF column);
- (1) dye affinity chromatography (preferably using a Blue Sepharose FF column);
- (2) hydrophobic interaction chromatography (HIC) (preferably using a Butyl 650M column);
- (3) reverse phase chromatography (RPC) (preferably using a Source 30 RPC column);
- (4) anion-exchange chromatography on a strongly basic anion exchange resin (preferably using a TMAE hicap resin); and
- (5) ultrafiltration (preferably with a membrane having a cut-off of 5 kD).

It may be desirable to subject the FSH sample to a step of nanofiltration, in particular as a virus clearance step; i.e. to reduce the risk of contamination of the FSH preparation with viruses or virus-like particles originating from the cell culture. Nanofiltration may be done at any stage of the purification process, however, it is particularly preferred to carry out nanofiltration after the $2^{nd}$ step of ion exchange chromatography, or after reverse phase chromatography or after hydrophobic interaction chromatography. Nanofiltration may be performed more than one time, for example it may be performed twice.

In a particularly preferred embodiment, the method of the invention comprises the following steps:
- (−1) Ultrafiltration (preferably with a membrane having a cut-off of at or about 8 kD),
- (0) anion-exchange chromatography (preferably with Q Sepharose FF),
- (1) dye affinity chromatography (preferably with Blue Sepharose FF),
- (2) hydrophobic interaction chromatography (HIC) (preferably with Butyl 650M),
- (3) reverse phase chromatography (RPC) (preferably with Source 30 RPC),
- (4) anion-exchange chromatography on a strongly basic anion-exchange resin (preferably TMAE hicap resin);
- (4') nanofiltration,
- (5) ultrafiltration (preferably with a membrane having a cut-off of 5 kD).

The advantage of the present invention is that the purification method is devoid of a cost intensive immuno-affinity chromatography step and provides anyhow a high degree of FSH purity and specific bioactivity. Also, the purified FSH of the present invention does not contain undesired impurities added by the immuno affinity chromatography (e.g. immunoglobulins leached from the resin)

Storage/Lyophilisation

The liquid composition resulting from the purification process as described above and containing purified FSH may be frozen for storage as is, or after purification, the eluate may be subjected to lyophilisation ("freeze-drying") to remove solvent. The resulting liquid or lyophilised product is termed "FSH Bulk".

FSH Formulations

FSH or an FSH variant of the invention or purified according to the method of the invention may be formulated for injection, either intramuscular or subcutaneous, preferably subcutaneous. The FSH formulation may be freeze-dried, in which case it is dissolved in water for injection just prior to injection. The FSH formulation may also be a liquid formulation, in which case it can be injected directly, without prior dissolution.

FSH formulation may be single dose or multiple dose. If it is multiple dose, it should preferably contain a bacteriostatic agent, such as, for example, benzyl alcohol, meta-cresol, thymol or phenol, preferably benzyl alcohol or meta-cresol. Single dose formulations may also comprise a bacteriostatic agent.

FSH of the invention may be formulated with known excipients and stabilizers, for example, sucrose and mannitol. It may also comprise an antioxidant, such as methionine. It may further comprise a surfactant, such as TWEEN (preferably TWEEN 20), or Pluronic (preferably Pluronic F68).

In a particularly preferred multidose formulation, FSH produced by the method of the invention is formulated by dissolving it in water for injection with sucrose, phosphate buffer (pH 7), Pluronic F68, methionine and meta-cresol or benzyl alcohol.

A particular preferred liquid multi-dose formulation of recombinant FSH for subcutaneous or intramuscular injection is the following:

Components of FSH multi-dose liquid formulations

| Component # | Description | 300 IU FSH | 450 IU FSH | 900 IU FSH |
|---|---|---|---|---|
| 1 | rhFSH (µg/cartridge) | 22.2 (305 IU) | 33.3 (458 IU) | 66.7 (916 IU) |
| 2 | Sucrose (mg/cartridge) | 30.0 | 45.0 | 90.0 |
| 3 | $NaH_2PO_4 \cdot H_2O$ (mg/cartridge) | 0.225 | 0.337 | 0.675 |
| 4 | $Na_2HPO_4 \cdot 2H_2O$ (mg/cartridge) | 0.555 | 0.832 | 1.665 |
| 5 | Pluronic F68 (mg/vial) | 0.050 | 0.075 | 0.150 |
| 6 | Methionine (mg/vial) | 0.050 | 0.075 | 0.150 |
| 7 | m-cresol (mg/vial) | 1.50 | 2.25 | 4.50 |
| 8 | pH | 7.0 | 7.0 | 7.0 |
| 9 | WFI | q.s. to 0.5 ml | q.s. to 0.75 ml | q.s. to 1.5 ml |

Indications

The FSH of the invention is suitable for use in all treatments where FSH is indicated. It is particularly suited for subcutaneous administration in ovulation induction, controlled ovarian hyperstimulation for assisted reproductive technologies, and in the treatment of oligospermia. It may be used in conjunction with other gonadotrophins, such as LH and hCG. It may also be used with further compounds which augment the response to FSH, such as clomiphene citrate, aromatase inhibitors, such as Anastrozole, Letrozole, Fadrozole and YM-511.

Sequences:

SEQ ID NO. 1: human glycoprotein α-subunit;

SEQ ID NO. 2: hFSH β-subunit

SEQ ID NO. 3: hFSH β-subunit variant 1

SEQ ID NO. 4: hFSH β-subunit variant 2

SEQ ID NO. 5: hFSH β-subunit variant 3

Follicle stimulating hormone, or FSH, as used herein refers to human FSH (hFSH) produced as a full-length mature protein. FSH is a dimer composed of the human glycoprotein alpha-subunit and the human FSH beta-subunit. The protein sequence of the human glycoprotein alpha subunit is provided in SEQ ID NO: 1, and the protein sequence of the human FSH beta subunit is given in SEQ ID NO: 2.

The use of the term "recombinant" refers to preparations of FSH that are produced through the use of recombinant DNA technology (see for example WO 85/01958). One example of a method of expressing FSH using recombinant technology is by transfection of eukaryotic cells with DNA sequences encoding an alpha and beta subunit of FSH, whether provided on one vector or on two vectors with each subunit having a separate promoter, as described in European patent nos. EP 0 211 894 and EP 0 487 512. The DNA encoding FSH may be a cDNA or it may contain introns. Another example of the use of recombinant technology to produce FSH is by the use of homologous recombination to insert a heterologous regulatory segment in operative connection to endogenous sequences encoding one or both of the subunits of FSH, as described in European patent no. EP 0 505 500 (Applied Research Systems ARS Holding NV). Also contemplated are methods such as those disclosed in WO 99/57263 (Transkaryotic Therapies), wherein one of the subunits is inserted heterologously into a cell, and the other subunit is expressed by activation of genomic sequences by insertion of a heterologous regulatory segment by homologous recombination. The method of the invention may be used to purify FSH expressed using any of these methods and other methods.

The expression "recombinant cell" refers to a cell produced by inserting heterologous DNA, including any of the above-mentioned methods of genetic manipulation.

Preferably the FSH is produced recombinantly in Chinese hamster ovary (CHO) cells transfected with a vector or vectors comprising DNA coding for the human glycoprotein alpha-subunit and the beta-subunit of FSH. DNA encoding the alpha and beta-subunits may be present on the same or different vectors.

The expression "FSH variant" is meant to encompass those molecules differing in amino acid sequence, glycosylation pattern or in inter-subunit linkage from human FSH but exhibiting FSH-activity. Examples include CTP-FSH, a long-acting modified recombinant FSH, consisting of the wild type α-subunit and a hybrid β-subunit in which the carboxy terminal peptide of hCG has been fused to the C-terminal of the β-subunit of FSH, as described in LaPolt et al.; Endocrinology; 1992, 131, 2514-2520; or Klein et al.; Development and characterization of a long-acting recombinant hFSH agonist; Human Reprod. 2003, 18, 50-56]. Also included is single chain CTP-FSH, a single chain molecule, consisting of the following sequences (from N-terminal to C-terminal):

| βFSH | βhCG-CTP(113-145) | αFSH |
|------|-------------------|------| wherein βFSH signifies the β-subunit of FSH, βhCG CTP (113-145) signifies the carboxy terminal peptide of hCG and αFSH signifies the α-subunit of FSH, as described by Klein et al. [*Pharmacokinetics and pharmacodynamics of single-chain recombinant human follicle-stimulating hormone containing the human chorionic gonadotrophin carboxyterminal peptide in the rhesus monkey; Fertility & Sterility;* 2002, 771248-1255]. Other examples of FSH variants include FSH molecules having additional glycosylation sites incorporated in the α- and/or β-subunit, as disclosed in WO 01/58493 (Maxygen), and FSH molecules with intersubunit S—S bonds, as disclosed in WO 98/58957. Further examples of FSH variants include chimeric molecules comprising sequences from FSH and sequences from hCG or LH, such as those described in WO 91/16922 and WO 92/22568.

The FSH variants referred to herein also include the carboxy terminal deletions of the beta subunit that are shorter than the full length mature protein of SEQ ID NO:2. Carboxy terminal deletions of the human beta subunit are provided in SEQ IDS NOS: 3, 4, and 5. It is understood that the carboxy terminal variants of the beta chain form complex with a known alpha subunit to form an FSH variant heterodimer.

In a preferred embodiment, the FSH is produced recombinantly in CHO cells, either in a serum or in a serum-free medium.

In a preferred embodiment, the purified FSH produced according to the method of the invention is suitable for subcutaneous administration, permitting self-administration by the patient.

The expression "crude recombinant FSH" refers to the cell culture supernatant from recombinant cells expressing FSH, before it has undergone any chromatographic step. The expression encompasses the raw form of the supernatant (as isolated from cells) as well as concentrated and/or filtered and/or ultrafiltered supernatant.

The term "biological activity" in relation to FSH activity, refers to the ability of an FSH formulation to elicit biological responses associated with FSH, such as ovarian weight gain in the Steelman-Pohley assay [Assay of the follicle stimulating hormone based on the augmentation with human chorionic gonadotrophin; Endocrinology; 1953, 53, 604-616], or follicular growth in a female patient. Follicular growth in a female patient can be evaluated by ultrasound, for example, in terms of the number of follicles having a mean diameter of at or about 16 mm on day 8 of stimulation. Biological activity is evaluated with respect to an accepted standard for FSH.

The LH content in an FSH preparation may be measured, for example, using an LH-specific immunoassay, such as the Delfia hLH Spec (Wallac Oy, Turku, Finland).

The term "specific activity", in reference to FSH, means the biological activity in IU of the preparation in a recognised biological assay for FSH, such as the Steelman Pohley bioassay [divided by the amount of protein, as determined by an assay for total protein content, such as the Lowry assay [O. H. Lowry, N. J. Rosebrough, A. L. Farr and R. J. Randall (1951) *J. Biol. Chem.* 193: 265; Hartree E. E. (1972). *Anal. Biochem.* 48: 422; J. R. Dulley and P. A. Grieve (1975) *Anal. Biochem.* 64: 136], the Bradford assay [Bradford, M. M. (1976) *Anal. Biochem.* 72, 248], or by absorbance at 280 nm.

Preferably, the FSH obtained by the invention has a specific activity of greater than at or about 8000 IU/mg, more preferably greater than at or about 9000 IU/mg, even more preferably greater than at or about 10000 IU/mg, even more preferably at or about 14000 IU/mg wherein biological activity is measured by the Steelman-Pohley bioassay and protein content is measured by SE-HPLC The FSH samples may be analysed in respect of their purity at various stages of the procedure using, for example, techniques such as those listed below:

r-hFSH Quantification/Free Alpha Subunit/purity/Oxidised Forms: RP-HPLC

As mentioned above, FSH is a heterodimeric glycoprotein, composed of an α- and a β-subunit. Some dissociation of the subunits can occur, and this can be monitored by looking at the amount of free α-subunit present in a sample. In addition, the FSH subunits may become oxidised. The oxidised contaminants can be quantified using RP-HPLC, while the free subunits may be assessed using SDS-PAGE.

r-hFSH Quantification: Immunoassay

FSH content in a sample can be determined using an immunoassay specific for FSH, such as the DELFIA FSH immunoassay.

Total Protein: Bradford Assay, Lowry Assay, Absorbance at 280 nm

As with any protein preparation, total protein content can be determined using techniques such as a Bradford assay, a Lowry Assay or by absorbance at 280 nm.

Isoforms Pattern: IEF

As mentioned above, FSH is a glycoprotein, having multiple oligosaccharide residues attached at various places on both subunits. The oligosaccharide residues may have different degrees of branching and may be capped with sialic acid residues. Sialic acid residues are negatively charged (at neutral pH). Differences in capping leads to heterogeneity, with a mixture of species having different isoelectric points (pI). This can be assessed using a technique that separates based on charge, such as isoelectric focussing (IEF)

Host Cell Protein (HCP)

Host cell protein can be analysed using an ELISA assay. For example, antibodies can be raised to a "mock culture", which is a culture of host cells without FSH gene.

EXAMPLES

The present invention will now be illustrated by means of 2 examples.

Figure 2:
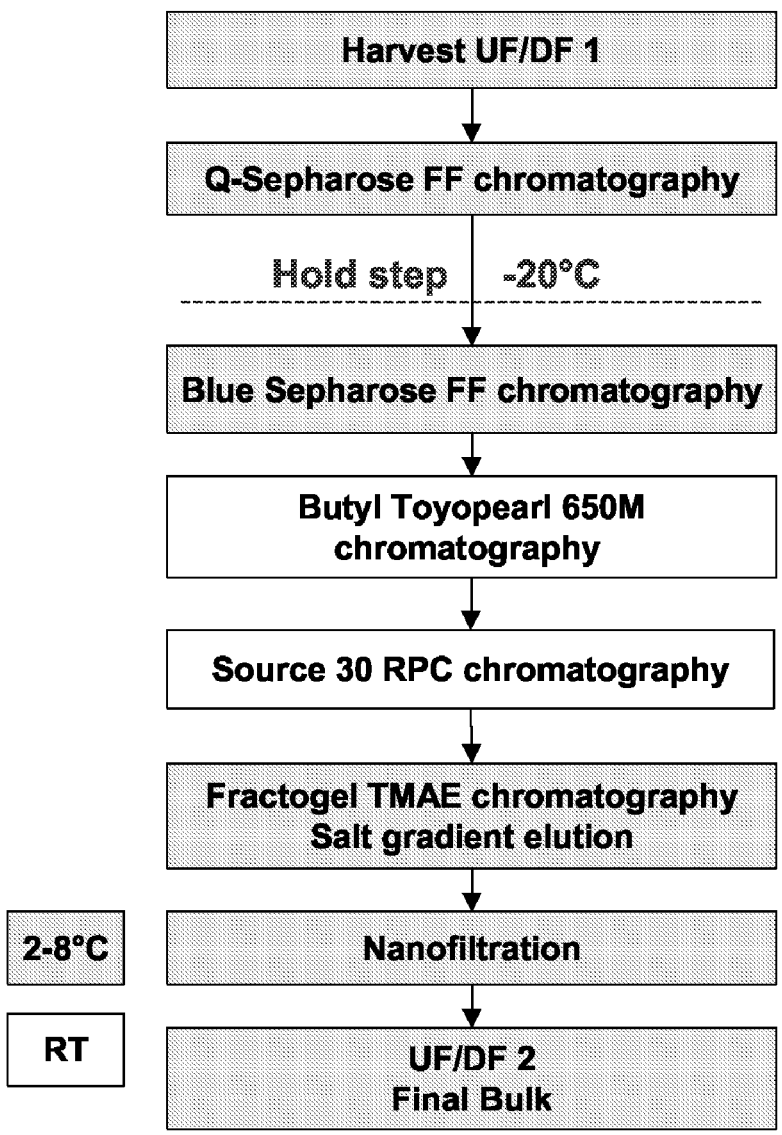
FIG. 2 shows a flow chart of a specific embodiment of the present invention, i.e. a process of purification comprising the steps of:
 ultrafiltration/diafiltration,
 anion-exchange chromatography,
 dye affinity chromatography,
 hydrophobic interaction chromatography,
 reverse phase chromatography,
 anion-exchange chromatography,
 nanofiltration,
 ultrafiltration/diafiltration.

Corresponding flow charts illustrating said 2 examples are presented in FIGS. 1 & 2. The resulting purified r-hFSH is termed "r-hFSH bulk".

Example 1

Of FIG. 1

Step (1): Dye Affinity Chromatography on Blue Sepharose

The FSH starting material for the purification is prepared from cell culture harvests containing recombinant FSH, i.e. FSH which was produced recombinantly in CHO cells, either in a serum or in a serum-free medium. The dye affinity chromatography column (Blue Sepharose FF resin) is first equilibrated with a low conductivity buffer at a pH of 8.5 containing L-methionine. The liquid containing the FSH is then applied directly to the resin. After the load, the unbound material is washed out using equilibration buffer. The FSH is finally eluted by flushing the column with Sodium phosphate buffer at pH 7.0, containing NaCl and L-methionine. The elution pool is directly processed to the next step. The step is performed at 2-8° C.

Step (2): Hydrophobic Interaction Chromatography (HIC) on Toyopearl Butyl 650 M

The Blue sepharose FF eluate from step (1) is loaded onto a Toyopearl Butyl 650M column equilibrated against a Sodium phosphate buffer, pH 7.0, containing Ammonium Sulfate and L-methionine. The unbound material is flushed out with equilibration buffer. The FSH is eluted with the same buffer, but with a reduced concentration of Ammonium Sulfate. The eluate is processed to the next step. The step is performed at RT Step (3): Reverse Phase on Source 30 RPC The HIC eluate (from step (2)) is first conditioned by addition of IPA (isopropanol). A Source 30RPC column is equilibrated against an ammonium acetate buffer, pH 7.6, containing L-methionine, and 2-propanol at a concentration equivalent to that of the conditioned load material. After flushing out the unbound material with equilibration buffer, the resin is washed with ammonium acetate buffer, pH 7.6, containing L-methionine, and an increased concentration of 2-propanol. The FSH is finally eluted by increasing further the concentration of 2-propanol. The elution pool is finally diluted under stirring, with water containing L-methionine. The diluted pool is processed to the next step. The step is performed at RT.

Upon following the above procedure, the factor of purification—i.e. the ratio of FSH purity in the purified sample versus the FSH purity in the starting material (crude FSH)—is at about 40.000.

Example 2

Of FIG. 2

Step (−1): Ultrafiltration/Diafiltration of Concentrated r-hFSH

All the operations were performed in refrigerated conditions (2-8° C.). The crude FSH forming the starting material for the purification is derived from cell culture harvests containing recombinant FSH.

Clarification

Crude r-hFSH was filtered through a 0.5 μm depth filter (such as Pall Profile II filters or equivalent).

Ultrafiltration

The clarified crude was first concentrated by ultrafiltration using a 10 KD polyether sulfone membrane. The concentrated retentate was then diafiltered against at least 5 diavolumes of borate buffer, pH 8.5 containing L-methionine as antioxidant. The conductivity and pH of the retentate were measured to monitor the progress of the diafiltration. The retentate was then concentrated further before draining the system. The ultra-filtration unit was finally flushed with diafiltration buffer and the rinsate mixed with the recovered retentate. The pool was progressed to the next step.

Filtration

The concentrated product was filtered through a 0.2 μm polyether sulphone filter (or equivalent).

Step (0): Anion Exchange on Q Sepharose FF

The filtered material was then applied to a strong anion exchange (Q-sepharose FF) resin equilibrated against Sodium Borate buffer, pH 8.5, containing L-methionine. After the load, the column was rinsed with equilibration buffer in order to flush all unbound material. The column was then eluted with Sodium Borate buffer pH 8.5, containing NaCl (to increase conductivity) and L-methionine (as an antioxidant). The elution pool collected was processed to the dye affinity chromatography.

Step (1): Dye affinity chromatography on Blue Sepharose

The dye affinity chromatography column (Blue Sepharose FF resin) was first equilibrated with the elution buffer from the Q-Sepharose FF step. The capture eluate was then applied directly to the resin. After the load, the unbound material was washed out using equilibration buffer. The FSH was finally eluted by flushing the column with Sodium phosphate buffer at pH 7.0, containing NaCl and L-methionine. The elution pool was directly processed to the next step. The step was performed at 2-8° C.

Step (2): Hydrophobic Interaction Chromatography on Toyopearl Butyl 650M

The Blue sepharose FF eluate was loaded onto a Toyopearl Butyl 650M column equilibrated against a Sodium phosphate buffer, pH 7.0, containing Ammonium Sulfate and L-methionine. The unbound material was flushed out with equilibration buffer. The FSH was eluted with the same buffer, but with a reduced concentration of Ammonium Sulfate. The eluate was processed to the next step. The step was performed at RT.

Step (3): Reverse Phase on Source 30 RPC

The HIC eluate (from step (2)) was first conditioned by addition of IPA (isopropanol). The Source 30RPC column was equilibrated against an ammonium acetate buffer, pH 7.6, containing L-methionine, and 2-propanol at a concentration equivalent to that of the conditioned load material. After flushing out the unbound material with equilibration buffer, the resin is washed with ammonium acetate buffer, pH 7.6, containing L-methionine, and an increased concentration of 2-propanol. The FSH is finally eluted by increasing further the concentration of 2-propanol. The elution pool is finally diluted under stirring, with water containing L-methionine. The diluted pool is processed to the next step. The step was performed at RT.

Step (4) Anion-Exchange Chromatography on Fractogel EMD TMAE hicap Resin

A Fractogel EMD TMAE hicap column was first equilibrated with Sodium Borate buffer, pH 8.5, containing L-methionine. The diluted post-RPC material (from step (3) was loaded onto the column. The unbound material was flushed out using equilibration buffer. The FSH is eluted from the column increasing the salt concentration in a linear fashion. The step was performed at 2-8° C.

Step (4') Nanofiltration

The eluate from the Fractogel EMD-TMAE step (4) was applied directly to a 20 nm nanofiltration device at a pressure of 3 bar under nitrogen. The filtrate is processed to the next step. The operation was performed at 2-8° C.

Step (5) Bulk Ultrafiltration

The nanofiltered FSH material was concentrated by tangential flow filtration on a 5 KD polyether sulphone membrane. When the retentate reached about half of the initial volume, the material was buffer-exchanged by diafiltration against WFI.

The Purity of the Samples

The purity of the FSH samples after the purification steps was determined

| Purification Step | Purity |
|---|---|
| Step (−1): Ultrafiltration/ Diafiltration | 19% FSH FSH determined by RP-HPLC Total protein content determined by Bradford Assay |
| Step (0): Anion Exchange on Q Sepharose FF | 44% FSH FSH determined by RP-HPLC Total protein content determined by Bradford |
| Step (1): Dye affinity chromatography on Blue Sepharose | 68% FSH FSH determined by RP-HPLC; Total protein content determined by Absorbance at 280 nm or about 420'000 ppm HCP FSH content determined by RP-HPLC; host cell protein content determined by ELISA |
| Step (2): Hydrophobic Interaction Chromatography on Toyopearl Butyl 650M | Amount of impurity: 3400 ppm FSH content determined by RP-HPLC; host cell protein content determined by ELISA |
| Step (3): Reverse Phase on Source 30 RPC | Amount of impurity: 170 ppm FSH content determined by RP-HPLC; host cell protein content determined by ELISA |
| Step (4) | Amount of impurity: <80 ppm |
| Anion-exchange chromatography on Fractogel EMD TMAE hicap resin | FSH content determined by RP-HPLC; host cell protein content determined by ELISA |

Biological Activity of Samples

The biological activity of the purified r-hFSH was measured using the Steelman-Pohley ovarian weight gain method. Specific activity was calculated using the biological activity divided by the FSH content as determined by an SE-HPLC method, as described below.

Specific activity of the final bulk obtained are typically between 10'000 to 17'000 IU/mg. Exemplary values for 2 samples of a final bulk FSH obtained following the method of Example 2 are given in Table 1.

TABLE 2

Specific activity of bulk purified rhFSH of the invention

| Analysis | Sample 1 | Sample 2 |
|---|---|---|
| Protein concentration by SE-HPLC (mg/ml) | 0.61 | 0.54 |
| Specific activity (Biological activity/SE-HPLC) | 12'600 IU/mg | 14'600 IU/mg |

The invention claimed is:

1. A method for purifying recombinant follicle stimulating hormone (FSH) or a FSH variant comprising subjecting a liquid containing FSH or a FSH variant to the following steps performed in order:
   (a) subjecting a liquid containing FSH or a FSH variant to anion-exchange chromatography and recovering an eluate containing FSH or FSH variant;
   (b) subjecting the eluate of step (a) to dye affinity chromatography and recovering an eluate containing FSH or a FSH variant;
   (c) subjecting the eluate of step (b) to hydrophobic interaction chromatography and recovering an eluate containing FSH or a FSH variant;
   (d) subjecting the eluate of step (c) to reverse phase chromatography and recovering an eluate containing FSH or a FSH variant; and
   (e) subjecting the eluate of step (d) to anion-exchange chromatography and recovering an eluate containing FSH or a FSH variant.

2. The method of claim 1 wherein the anion-exchange chromatography step of step (e) is performed using a resin comprising trimethylaminoethyl groups.

3. The method of claim 2, wherein the anion-exchange chromatography step of step (e) is performed using borate buffer and a gradient of increasing NaCl concentration.

4. The method of claim 1, further comprising nanofiltration after the anion chromatography step of step (e).

5. A method for purifying human recombinant FSH comprising subjecting a liquid containing FSH to:
   (a) ultrafiltration of said liquid and recovering a retentate;
   (b) subjecting said retentate to anion exchange chromatography on a resin comprising quaternary ammonium groups and eluting a first eluate with a buffer comprising borate/NaCl and L-methionine at a pH of, or about, 8.5;
   (c) subjecting the first eluate to a step of dye affinity chromatography on a resin comprising cibacron blue and eluting a second eluate with a buffer comprising phosphate, NaCl and L-methionine at a pH of, or about, 7;
   (d) subjecting the second eluate to hydrophobic interaction chromatography on a resin comprising butyl groups and eluting a third eluate with a buffer comprising phosphate, ammonium sulfate and, L-methionine, at a pH of, or about, 7;
   (e) subjecting the third eluate to reverse phase chromatography on a sizing resin with a buffer comprising ammonium acetate, L-methionine and 2-propanol at a pH of, or about, 7.6 and eluting a fourth;
   (f) subjecting the fourth eluate to anion-exchange chromatography on a resin comprising triethylaminoethyl groups with a buffer comprising borate and L-methionine at a pH of, or about, 8.5, and NaCl and eluting a fifth eluate;
   (g) subjecting the fifth eluate to nanofiltration to form a permeate; and
   (h) subjecting the permeate of step (g) to ultrafiltration.

* * * * *

UNITED STATES PATENT AND TRADEMARK OFFICE
CERTIFICATE OF CORRECTION

PATENT NO. : 7,741,455 B2
APPLICATION NO. : 11/575833
DATED : June 22, 2010
INVENTOR(S) : Pascal Valax et al.

It is certified that error appears in the above-identified patent and that said Letters Patent is hereby corrected as shown below:

Column 1,
Line 66, "$A_{1\,cm}^{280}$" should read --$A^{280}_{1cm}$--.

Column 2,
Line 42, "$A_{1\,cm}^{280}$" should read --$A^{280}_{1cm}$--.

Column 4,
Lines 35-36, "and then and optionally" should read --and then optionally--.

Column 9,
Line 25, "FSH formulation" should read --The FSH formulation--.
Line 31, "FSH of the" should read --The FSH of the--.

Column 11,
Line 15, "771248-1255]" should read --77, 1248-1255]--.
Lines 60-61, "bioassay [divided" should read --bioassay, divided--.

Column 12,
Lines 58-59, "Example 1      should read      --Example 1 (cf Figure 1)--.
                 Of FIG. 1"

Column 13,
Line 18, "at RT" should read --at RT.--.
Lines 39-40, "Example 2      should read      --Example 2 (cf Figure 2)--.
                 Of FIG. 2"

Column 14,
Line 51, "(from step (3)" should read --(from step (3))--.

Column 15,
Line 3, "determined" should read --determined:--.

Signed and Sealed this

Twelfth Day of October, 2010

David J. Kappos
*Director of the United States Patent and Trademark Office*